US00PP34606P2

(12) United States Plant Patent
Horvath

(10) Patent No.: US PP34,606 P2
(45) Date of Patent: Sep. 20, 2022

(54) ***PENNISETUM ALOPECUROIDES* PLANT NAMED 'PURE ENERGY'**

(50) Latin Name: *Pennisetum alopecuroides*
Varietal Denomination: Pure Energy

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/300,656

(22) Filed: Sep. 14, 2021

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

(56) References Cited

U.S. PATENT DOCUMENTS

PP31,362 P2 * 1/2020 Horvath ..... A01H 6/4654 Plt./384

* cited by examiner

*Primary Examiner* — Susan McCormick Ewoldt

(57) ABSTRACT

A new, distinct *Pennisetum alopecuroides* plant as shown and described, characterized by yellow-green foliage RHS color 153 A-D inflorescences on 70 cm stems that start in mid-August in northern Illinois.

1 Drawing Sheet

Figure 1:
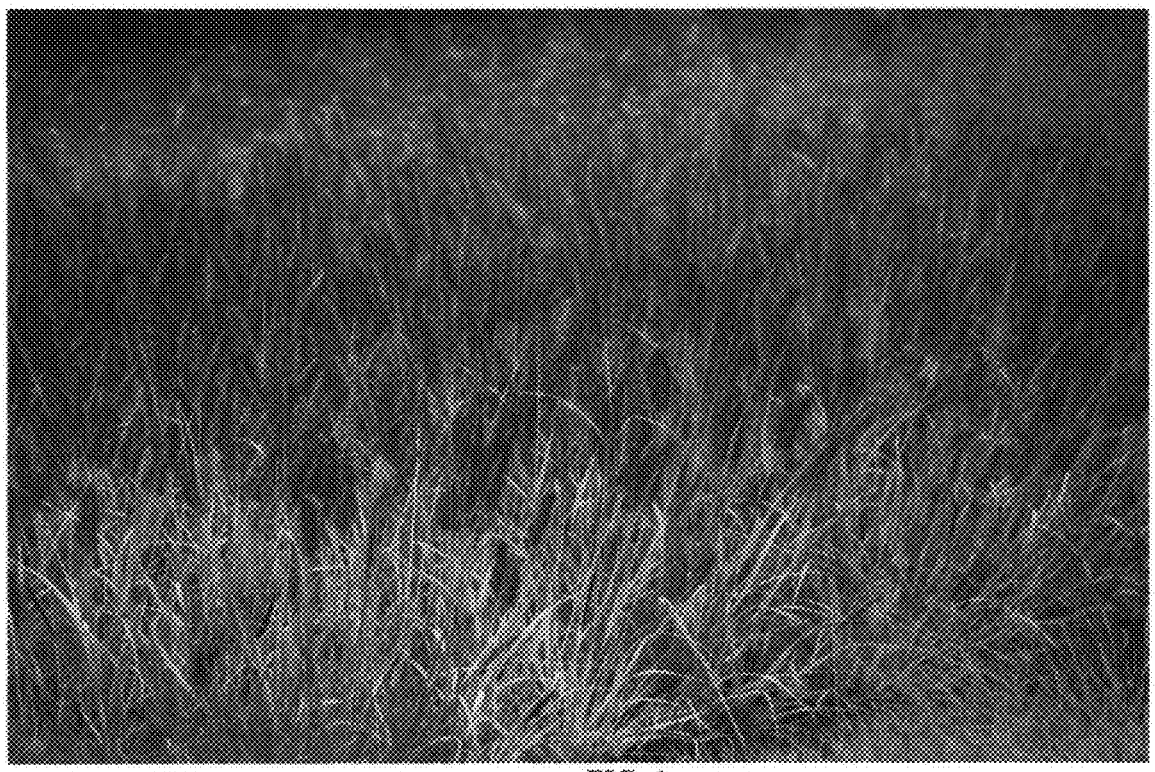

Latin name: *Pennisetum alopecuroides*.
Cultivar name: 'Pure Energy'.

BACKGROUND OF THE INVENTION

The present invention relates to a new form of *Pennisetum alopecuroides* plant named 'Pure Energy'. 'Pure Energy' is a seedling of an unnamed *Pennisetum alopecuroides*, not patented., characterized by yellow-green foliage RHS color 153 A-D, inflorescence RHS color 145 B, on 70 cm stems that start in mid-August in northern Illinois. The new plant is the result of a breeding program taking place at a wholesale perennial nursery since 2001. The seedling was grown by the inventor at a wholesale perennial nursery in Hebron, Ill. in 2018. The selection of the new plant was due to its yellow-green colored foliage, RHS 153 A-D, inflorescence RHS color 145 B on 70 cm stems that start in mid-August in northern Illinois. Asexual, vegetative division propagation has been the only means of reproduction. Propagation has taken place at a wholesale perennial nursery Hebron, Ill. in 2011. To date these plants have remained uniform in height. The new *Pennisetum* has shown to be stable and identical in reproduction to the parent after making over 500 vegetative divisions from 2018 to 2019. No plants of the new *Pennisetum alopecuroides* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

In the following description, color references are made to The Royal Horticultural Society Colour Chart. The new

*Pennisetum alopecuroides* plant named 'Pure Energy' has shown the characteristic of yellow-green foliage RHS color 153 A-D, inflorescence RHS color 145 B, on 70 cm stems that start in mid-August in northern Illinois.

The parent plants were not available for comparison. Plants of the new *Pennisetum* can be compared to plants of *Pennisetum alopecuroides* 'Red Head', not patented. 1. The new *Pennisetum* has a height of 70 cm compared to the height of *Pennisetum alopecuroides* 'Red Head' which has a height of 120 cm. 2. The new *Pennisetum* has an inflorescence length of 13 cm compared to *Pennisetum alopecuroides* 'Red Head' which has an inflorescence length of 20 cm.

Plants of the new *Pennisetum* can be compared to plants of *Pennisetum alopecuroides* 'Hameln' not patented. 1. The new *Pennisetum* has a height of 70 cm compared to the height of *Pennisetum alopecuroides* 'Hameln' which has a height of 90 cm. 2. The new *Pennisetum* has an inflorescence length of 13 cm compared to *Pennisetum alopecuroides* 'Hameln' which has an inflorescence length of 10 cm. 3. The new *Pennisetum* has a yellow-green inflorescence color compared to *Pennisetum alopecuroides* 'Hameln' which has a tan inflorescence color.

Plants of the new *Pennisetum* can be compared to plants of *Pennisetum alopecuroides* 'Mondry', not patented. 1. The new *Pennisetum* has a height of 70 cm compared to the height of *Pennisetum alopecuroides* 'Mondry' which has a height closer to 60 cm. 2. The new *Pennisetum* has a mid-August bloom time compared to *Pennisetum alopecuroides* 'Moudry' which typically blooms in October.

DESCRIPTION OF PHOTOGRAPHS

FIG. 1. Shows a group of potted 1 gallon plants flowering in Hebron, Ill. USA.

Figure 2:
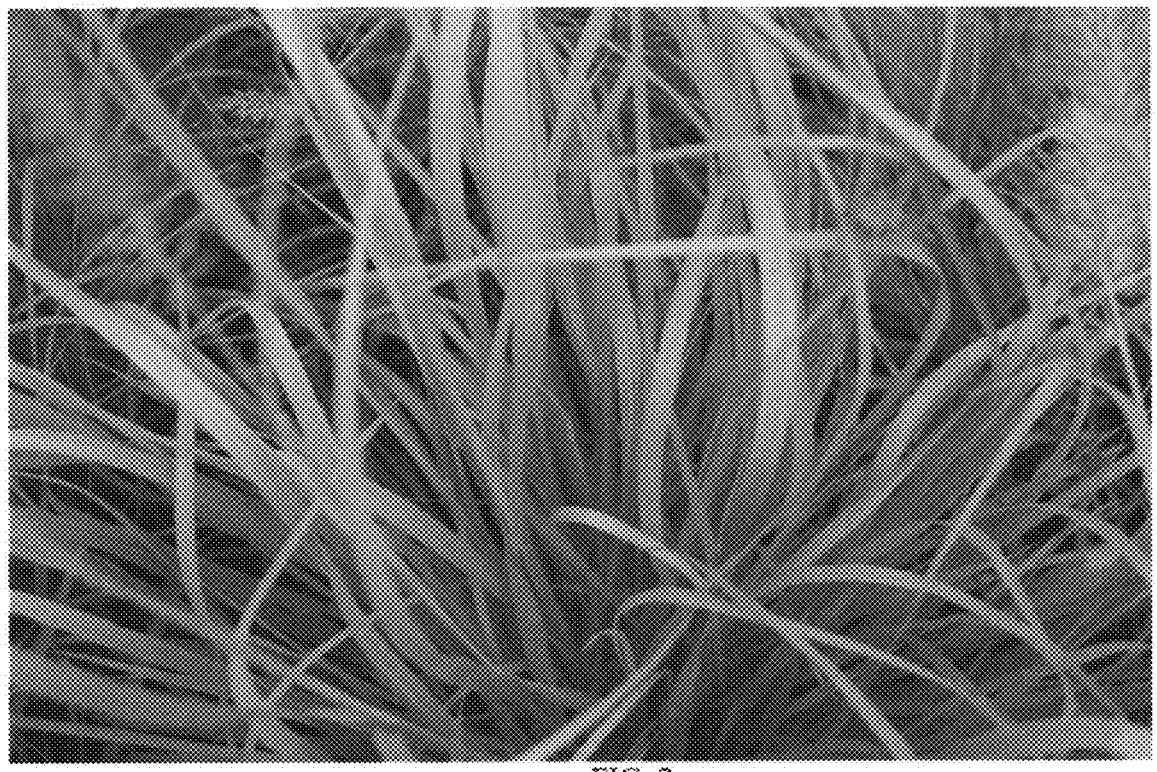

FIG. 2. Shows a close up of the foliage in Hebron, Ill. USA.

DETAILED BOTANICAL DESCRIPTION

In the following description, color references are made to The Royal Horticultural Society Colour Chart (2001). The plant herein described is a one year old, three gallon specimen grown. in full sun and irrigated in Hebron, Ill.

Botanical classification: *Pennisetum alopecuroides* cultivar 'Pure Energy'.

Parentage: *Pennisetum alopecuroides* unnamed seedling selections.

Propagation: Vegetative division.

Plant description: Overall habit of the new *Pennisetum* is strongly clumping mounds with upright stems topped by yellow-green colored inflorescences in mid-August. Vigor is moderate to fast.

*Plant height.*—70 cm.

*Plant width.*—60 cm.

*Stem diameter.*—6 mm.

*Stem color.*—Between 146 B to 145 C.

Foliage:

*Type.*—Deciduous, grass growing in culms.

*Shape.*—Blade.

*Petiole.*—None.

*Blade length.*—25 cm average, ranging from 15-33 cm.

*Width.*—9 mm.

*Adaxial leaf description.*—The leaf color is RHS color 153 A-D.

*Abaxial leaf description.*—The leaf color is RHS color 153 A-D.

*Basal leaf sheath color.*—some red tips 182 A on top, 166 C bottom.

*Leaf sheath.*—Glabrous.

*Auricles.*—Not present.

*Ligules.*—As wide as the leaf blade, up to 1 mm tall, color close to 159 B.

*Collars.*—Continuous, as wide as the leaf blade, leis than 1 mm tall, color close to 159 B. Leaf buds are folded in the bud stage.

*Rhizomes or stolons.*—None. The attitude of the tiller on the can is erect, 20 degrees from the culm. The culm node is glabrous and color at the node is close to 146 B to C.

*Internode.*—Length 7-19 cm, 7 cm short at base, avg 13 cm above that.

*Culm diameter and color at the internode.*—6 mm, close to 146 B & C.

*Fall leaf color.*—20 A.

Flower inflorescence:

*Number of spike bearing tillers in the culms.*—54.

*Inflorescence type.*—Terminal bristled spike.

*Immature floret color.*—145 B.

*Individual floret size.*—1-2 mm across, 6 mm tall.

*Anther coloration and size.*—N200 A, 2-3 mm long, 0.5-1 mm wide.

*Stigma color and size.*—Close to N199 D, 8 mm long, 0.5 mm wide.

*Glume color and size.*—Close to 199 D, 2 mm, less than 1 mm wide.

*Bristle size.*—30 mm long, less than 1 mm wide.

*Bristle color.*—N200 A.

*Caryopsis color.*—145 A, shape — elliptic.

*Overall inflorescence spike size.*—5 cm wide, 31 cm long.

*Flower number.*—Approximately 42 florets per mature spike measuring 5 cm wide, 13 cm long.

*Fertility.*—Self-fertile, Fertile with 3 Anthers and 3 Stamens, 1 Stigma.

*Blooming habit.*—Terminal bristled spike on up to 70 cm stems.

*Bloom period and duration.*—Mid-August into October.

*Scent.*—No scent noticed.

*Roots.*—Stiff, fibrous, and freely branching.

*Fruit.*—Seed identical, to the species except size is a slightly smaller.

Disease resistance: Plants are not susceptible to any major pests or diseases.

I claim:

1. A new, distinct *Pennisetum alopecuroides* plant as shown and described, characterized by yellow-green foliage RHS color 153 A-D, inflorescence RHS color 145 B ort 70 cm stems that start in mid-August in northern Illinois.

* * * * *